United States Patent
Yoo

(10) Patent No.: US 6,251,428 B1
(45) Date of Patent: Jun. 26, 2001

(54) PREPARATION OF AQUEOUS CLEAR SOLUTION DOSAGE FORMS WITH BILE ACIDS

(76) Inventor: Seo Hong Yoo, 537 Spencer Dr., Wyckoff, NJ (US) 07481

(*) Notice: Subject to any disclaimer, the term of this patent is extended or adjusted under 35 U.S.C. 154(b) by 0 days.

(21) Appl. No.: 09/357,549

(22) Filed: Jul. 20, 1999

Related U.S. Application Data

(60) Provisional application No. 60/094,069, filed on Jul. 24, 1998.

(51) Int. Cl.[7] .................................................. A61K 9/66

(52) U.S. Cl. ........................ 424/455; 424/456; 424/479

(58) Field of Search ................................... 424/455, 456, 424/479

(56) References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,327,725 | 5/1982 | Cortese et al. | 128/260 |
| 4,681,876 | 7/1987 | Marples et al. | 514/182 |
| 5,057,321 | 10/1991 | Edgren et al. | 424/413 |
| 5,149,537 | 9/1992 | Azria et al. | 424/436 |
| 5,260,074 | 11/1993 | Sipos | 424/497 |
| 5,300,300 | 4/1994 | Egidio et al. | 424/456 |
| 5,302,398 | 4/1994 | Egidio et al. | 424/474 |
| 5,302,400 | 4/1994 | Sipos | 424/494 |
| 5,310,560 | 5/1994 | Widauer | 424/451 |
| 5,324,514 | 6/1994 | Sipos | 424/94.63 |
| 5,380,533 | 1/1995 | Egidio et al. | 424/456 |
| 5,470,581 | 11/1995 | Grillo et al. | 424/479 |
| 5,484,776 | 1/1996 | Racz et al. | 514/54 |
| 5,534,505 | 7/1996 | Widauer | 514/169 |
| 5,578,304 | 11/1996 | Sipos | 424/94.1 |
| 5,641,767 | 6/1997 | Wess et al. | . |
| 5,653,987 | 8/1997 | Modi et al. | 424/400 |
| 5,686,588 | 11/1997 | Yoo | . |
| 5,843,929 | 12/1998 | Larson et al. | 514/182 |
| 5,858,998 | 1/1999 | Leuschner | 514/171 |
| 5,863,550 | 1/1999 | Maeda et al. | 424/423 |

FOREIGN PATENT DOCUMENTS

| | | |
|---|---|---|
| 0312052 | 4/1989 | (EP) . |
| 55-022616 | 2/1980 | (JP) . |
| 62-153220 | 7/1987 | (JP) . |

OTHER PUBLICATIONS

Matthew J. Mollan, Jr. et al., "One of Aqueous Soluble Starch Conversion Products", Maltodextrin, N/D, pp. 308–349. 1995.

"Maltrin® Maltodextrins & Corn Syrup Solids Chemical and Physical Properties", GPC Technical Bulletin, TB31–021296, Grain Processing Corp., Muscatine, Iowa, N/D, Brochure + 4 pages. 1999.

"Saccharide Composition Typical Carbohydrate Profiles", GPC Technical Bulletin TB30–021296, Grain Processing Corp., Muscatine, Iowa, N/D, 1 page.

Martin C. Carey, MD et al., "Micelle Formation by Bile Salts Physical–Chemical and Thermodynamic Considerations", Arch. Intern. Med., vol. 130 (Oct. 1972) pp. 506–527.

Hirotsune Igimi et al., "pH–Solubility Relations of Chenodeoxycholic and Ursodeoxycholic Acids: Physical–Chemical Basis for Dissimilar Solution and Membrane Phenomena", J. of Lipid Research, vol. 21 (1980) pp. 72–90.

Daniel Hollander et al., "Intestinal Absorption of Aspirin, Influence of pH, Taurocholate, Ascorbate and Ethanol", J. Lab. Clin. Med., vol. 98, No. 4 (Oct. 1981) pp. 591–595.

Shinichiro Hirai et al., "Effect of Surfactants on the Nasal Absorption of Insulin in Rats", International J. of Pharmaceutics, vol. 9 (1981) pp. 165–171.

Shinichiro Hirai et al., "Mechanisms for the Enhancement of the Nasal Absorption of Insulin by Surfactants", International J. of Phamaceutics, vol. 9 (1981) pp. 173–184.

M. O. Reynier et al., "Comparative Effects of Cholic, Chenodeoxycholic, and Ursodeoxycholic Acids on Micellar Solubilization and Intestinal Absorption of Cholesterol", J. of Lipid Research, vol. 22 (1981) pp. 467–473.

Shinya Nagamatsu, "Phase I Clinical Study of Ursodesoxycholic Acid", Jpn. Pharmacol. Ther., vol. 25, No. 6 (1997) pp. 145–159.

M. A. Hammad et al., "Solubility and Stability of Tetrazepam in Mixed Micelles", European J. of Pharmaceutical Sciences, vol. 7 (1998) pp. 49–55.

M. A. Hammad, B. W. Müller, Increasing Drug Solubility by Means of Bile Salt–Phosphatidylcholine–Based Mixed Micelles, European J. of Pharmaceutics and Biopharmaceutics. vol. 46 (1998) pp. 361–367.

Aad Verrips et al., "Effect of Simvastatin in Addition to Chenodeoxycholic Acid in Patients with Cerebrotendinous Xanthomatosis", Metabolism, vol. 48, No. 2 (Feb. 1999) pp. 233–238.

Pietro Invernizzi et al., "Differences in the Metabolism and Disposition of Ursodeoxycholic Acid and of its Taurine–Conjugated Species in Patients with Primary Biliary Cirrhosis", Hepatology, vol. 29, No. 2 (Feb. 1999) pp. 320–327.

(List continued on next page.)

Primary Examiner—Marianne M. Cintins
Assistant Examiner—Vickie Kim
(74) Attorney, Agent, or Firm—Baker Botts L.L.P.

(57) ABSTRACT

Compositions for pharmaceutical and other uses for preparing clear aqueous solutions containing bile acids which do not form precipitates over selected ranges of pH values of the aqueous solution and methods of making such solutions. The compositions of the invention comprise water; a bile acid in the form of a bile acid, bile acid salt, or a bile acid conjugated with an amine by an amide linkage; and a high molecular weight aqueous soluble starch conversion product. The composition remains in solution without forming a precipitate over a range of pH values and, according to one embodiment, remains in solution for all pH values obtainable in an aqueous system. The composition, according to some embodiments, may further contain a pharmaceutical compound in a pharmaceutically effective amount.

35 Claims, 2 Drawing Sheets

OTHER PUBLICATIONS

George C. Na, "Cloud Point of Nonionic Surfactants: Modulation with Pharmaceutical Excipients", Pharmaceutical Research, vol. 16, No. 4 (1999) pp. 562–568.

Maria Leuschner et al., "Liver, Pancreas and Biliary Tract, Oral Budesonide and Ursodeoxycholic Acid for Treatment of Primary Biliary Cirrhosis: Results of a Prospective Double–Blind Trial", Gastroenterology, vol. 117 (1999) pp. 918–925.

Mohamed A. Hammad et al., "Solubility and Stability of Lorazepam in Bile Salt/Soya Phosphatidylcholine–Mixed Micelles", Drug Development and Industrial Pharmacy, vol. 25, No. 4 (1999) pp. 409–417.

F. Lanzarotto et al., "Effect of Long–Term Simvastatin Administration as an Adjunct to Ursodeoxycholic Acid: Evidence for a Synergistic Effect on Biliary Bile Acid Composition but Not on Serum Lipids in Humans", GUT, vol. 4 (1999) pp. 552–556.

Juha Sinisalo et al., "Ursodeoxycholic Acid and Endothelial–Dependent, Nitric Oxide–Independent Vasodilatation of Forearm Resistance Arteries in Patients with Coronary Heart Disease", Br. J. Clin. Pharamcol., vol. 47 (1999) pp. 661–665.

Moses, Alan C., et al., *Diabetes*, 32, 1040–1047 (1983).

Ziv E. et al., *Biochemical Pharmacology*, 32(5), 773–776 (1983).

Gordon, G.S. et al., *Proc. Nat'l. Acad. Sci. USA*, 82, 7419–7423 (1985).

Parquet, M. et al., *J. of Clinical Invest.*, 15, 171–178 (1985).

Miyajima, K. et al., *Chem. Pharm. Bull.*, 34(3), 1395–1398 (1986).

Tan, X. and Lindenbaum, S., *Int'l J. of Pharmaceutics*, 74, 127–135 (1991).

Wacker Biochem Corp., advertisement, *C&EN*, 31 (Apr. 12, 1999).

Marcia J. Armstrong et al., "The Hydrophobic–Hydrophilic Balance of Bile Salts. Inverse Correlation between Reverse–Phase High Performance Liquid Chromatographic Mobilities and Micellar Cholesterol–Solubilizing Capacities", J. of Lipid Research, vol. 23 (1982) pp. 70–80.

Mauro Podda et al., "Gallstone Dissolution After 6 Months of Ursodeoxycholic Acid (UDCA): Effectiveness of Different Doses", J. Int. Med. Res., vol. 10 (1982) pp. 59–63.

Alan C. Moses et al., "Insulin Administered Intranasally as an Insulin–Bile Salt Aerosol Effectiveness and Reproducibility in Normal and Diabetic Subjects", Diabetes, vol. 32 (Nov. 1983) pp. 1040–1047.

E. Ziv et al., "Bile Salts Facilitate the Absorption of Heparin from the Intestine", Biochemical Pharmacology, vol. 32, No. 5 (1983) pp. 773–776.

P. L. Zentler–Munro et al., "Effect of Intrajejunal Acidity on Aqueous Phase Bile Acid and Lipid Concentrations in Pancreatic Steatorrhoea Due to Cystic Fibrosis", GUT, vol. 25 (1984) pp. 500–507.

Karl Müller, "Structural Aspects of Bile Salt–Lecithin Mixed Micelles", Hepatology, vol. 4, No. 5 (1984) pp. 134S–137S.

Teruo Murakami et al., "Effect of Bile Salts on the Rectal Absorption of Sodium Ampicillin in Rats", Chem. Pharm. Bull., vol. 32, No. 5 (1984) pp. 1948–1955.

G. S. Gordon et al., "Nasal Absorption of Insulin: Enhancement by Hydrophobic Bile Salts", Proc. Natl. Acad. Sci., vol. 82 (Nov. 1985) pp. 7419–7423.

M. Parquet et al., "Bioavailability, Gastrointestinal Transit, Solubilization and Faecal Excretion or Ursodeoxycholic Acid in Man", European J. of Clinical Investigation, vol. 15 (1985) pp. 171–178.

A. L. Golub, Ph.D. et al., "Physiologic Considerations in Drug Absorption from the Gastrointestinal Tract", J. Allergy Clin. Immunol., vol. 78, No. 4, Part 2 (Oct. 1986) pp. 689–694.

Koichiro Miyajima et al., "Interaction of β–Cyclodextrin with Bile Salts in Aqueous Solutions", Chem. Pharm. Bull., vol. 34, No. 3 (1986) pp. 1395–1398.

Carla Colombo, MD, et al., "Effects of Ursodeoxycholic Acid Therapy for Liver Disease Associated with Cystic Fibrosis", J. of Pediatrics, vol. 117, No. 3 ( Sep. 1990) pp. 482–489.

Olivier Chazouilleres et al., "Ursodeoycholic Acid for Primary Sclerosing Cholangitis", J. of Hepatology, vol. 11(1990) pp. 120–123.

Marsha Y. Morgan, "Branched Chain Amino Acids in the Management of Chronic Liver Disease Facts and Fantasies", J. of Hepatology, vol. 11 (1990) pp. 133–141.

Xinyi Tan et al., "Studies on Complexation between β–Cyclodextrin and Bile Salts", International J.of Pharmaceutics, vol. 74 (1991) pp. 127–135.

Carla Colombo et al., "Ursodeoxycholic Acid Therapy in Cystic Fibrosis–associated Liver Disease: A Dose–response Study", Hepatology, vol. 16, No. 4 (1992) pp. 924–930.

Jeff De Caprio et al., "Bile Acid and Sterol Stabilization in 2–Hydroxypropyl–β–Cyclodextrin", Journal of Lipid Research, vol. 33 (1992) pp. 441–443.

Siegfried Walker et al., "Intestinal Absorption of Ursodeoxycholic Acid in Patients with Extrahepatic Biliary Obstruction and Bile Drainage", Gastroenterology, vol. 102, No. 3 (1992) pp. 810–815.

Andrew D. McLeod et al., "Synthesis and Chemical Stability of Glucocorticoid–Dextran Esters: Potential Prodrugs for Colon–Specific Delivery", International J. of Pharmaceutics,vol. 92 (1993) pp. 105–114.

Scott L. Myers et al., "Solid–State Emulsions: The Effects of Maltodextrin on Microcrystalline Aging", Pharmaceutical Research, vol. 10, No. 9 (1993) pp. 1389–1391.

Gerrit H. P. Te Wierik et al., "Preparation, Characterization, and Pharmaceutical Application of Linear Dextrins, I. Preparation and Characterization of Amylodextrin, Metastable Amylodextrins, and Metastable Amylose", Pharmaceutical Research, vol. 10, No. 9 (1993) pp. 1274–1279.

Gerritt H. P. Te Wierik et al., "Preparation, Characterization, and Pharmaceutical Application of Linear Dextrins. II. Complexation and Dispersion of Drugs with Amylodextrin by Freeze–Drying and Kneading", Pharmaceutical Research, vol. 10, No. 9 (1993) pp. 1280–1284.

Jennifer B. Dressman et al., "Gastrointestinal Parameters that Influence Oral Medications", J. of Pharmaceutical Sciences, vol. 82, No. 9 ( Sep. 1993) pp. 857–872.

Thorsteinn Loftsson et al., "The Effect of Cyclodextrins on the Solubility and Stability of Medroxyprogesterone Acetate and Megestrol Acetate in Aqueous Solution", International J. of Pharmaceutics, vol. 98 (1993) pp. 225–230.

G. H. P. Te Wierik et al., "Preparation, Characerization and Pharmaceutical Application of Linear Dextrins: IV. Drug Release from Capsules and Tablets Containing Amylodextrin", International J. of Pharmaceutics, vol. 98 (1993) pp. 219–224.

Andrew D. McLeod et al., "Glucocorticoid–Dextran Conjugates as Potential Prodrugs for Colon–Specific Delivery: Steady–State Pharmacokinetics in the Rat", Biopharmaceutics & Drug Disposition, vol. 15 (1994) pp. 151–161.

Aldo Roda et al., "Improved Intestinal Absorption of an Enteric–Coated Sodium Ursodeoxycholate Formulation", Pharmaceutical Research, vol. 11, No. 5 (1994) pp. 642–647.

Kurt Einarsson, Ed., "Treatment with Ursodeoxycholic Acid in Clinical Hepatology", Proceedings of a Workshop Held 3 and 4 Feb. 1994 in Goteborg, Sweden, Scandinavian Univeristy Press (1994) pp. 1–72.

Keith D. Lindor et al., "The Combination of Ursodeoxycholic Acid and Methotrexate for Patients with Primary Biliary Cirrhosis: The Results of a Pilot Study", Hepatology, vol. 22, No. 4 (Oct. 1995) pp. 1158–1162.

"Pharmaceutical Necessities", Remington: The Science and Practice of Pharmacy, Mack Printing Co., Easton, Pennsylvania (1995) pp. 1409–1410.

R. A. Jorgensen, "Characteristics of Patients with a Complete Biochemical Response to Ursodeoxycholic Acid", GUT vol. 36 (1995) pp. 935–938.

A. Benjamin Suttle and Kim L. R. Brouwer, "Regional Gastrointestinal Absorption of Ranitidine in the Rat", Pharmaceutical Research, vol. 12, No. 9 (1995) pp. 1311–1315.

Patrizia Simoni et al., "Bioavailability Study of a New, Sinking, Enteric–Coated Ursodeoxycholic Acid Formulation", Pharmacological Research, vol. 31, No. 2 (1995) pp. 115–119.

Cecilia M. P. Rodrigues et al., "The Site–Specific Delivery of Ursodeoxycholic Acid to the Rat Colon by Sulfate Conjugation", Gastroenterology, vol. 109 (1995) pp. 1835–1844.

R. Panini et al., "Improvement of Ursodeoxycholic Acid Bioavailability by 2–Hydroxypropyl–$\beta$–Cyclodextrin Complexation in Healthy Volunteers", Pharmacological Research, vol. 31, No. 314 (1995) pp. 205–209.

Ann W. Newman et al., "Starch", Analytical Profiles of Drug Substances, Bristol–Myer Squibb Pharmaceutical Research Institute, New Brunswick, NJ (1996) pp. 523–577.

R. Panini et al., "The Influence of 2–Hydroxypropyl–$\beta$–Cyclodextrin on the Haemolysis Induced by Bile Acids", J. Pharm. Pharmacol., vol. 48 (1996) pp. 641–644.

Andrea Crosignani, et al., "Clinical Pharamcokinetics of Therapeutic Bile Acids", Clin. Pharmacokinet, vol. 30, No. 5 (May, 1996) pp. 333–358.

Nicholas A. Buckley et al., "Controlled Release Drugs in Overdose Clinical Consideration", Drug Safety, vol. 12, No. 1 (1996) pp. 73–82.

PREPARATION OF AQUEOUS CLEAR SOLUTION DOSAGE FORMS WITH BILE ACIDS

SPECIFICATION

This application claims the benefit of provisional application No. 60/094,069, filed Jul. 24, 1998, which provisional application is incorporated herein by reference.

BACKGROUND OF THE INVENTION

Bile acids salts which are organic acids derived from cholesterol are natural ionic detergents that play a pivotal role in the absorption, transport, and secretion of lipids. In bile acid chemistry, the steroid nucleus of bile acids salts has the perhydrocyclopentano phenanthrene nucleus common to all perhydrosteroids. Distinguishing characteristics of bile acids include a saturated 19-carbon sterol nucleus, a beta-oriented hydrogen at position 5, a branched, saturated 5-carbon side chain terminating in a carboxylic acid, and an alpha-oriented hydroxyl group in the 3-position. The only substituent occurring in most natural bile acids is the hydroxyl group In most mammals the hydroxyl groups are at the 3, 6, 7 or 12 positions.

The common bile acids differ primarily in the number and orientation of hydroxyl groups on the sterol ring. The term, primary bile acid refers to these synthesized de novo by the liver. In humans, the primary bile acids include cholic acid (3α, 7α, 12α-trihydroxy-5β-cholanic acid) ("CA") and chenodeoxycholic acid (3α, 7α-dihydroxy-5β-cholanic acid) ("CDCA"). Dehydroxylation of these bile acids by intestinal bacteria produces the more hydrophobic secondary bile acids, deoxycholic acid (3α, 12α-dihydroxy-5β-cholanic acid) ("DCA") and lithocholic acid (3α-hydroxy-5β-cholanic acid) ("LCA"). These four bile acids CA, CDCA, DCA, and LCA, generally constitute greater than 99 percent of the bile salt pool in humans. Secondary bile acids that have been metabolized by the liver are sometimes denoted as tertiary bile acids.

Keto-bile acids are produced secondarily in humans as a consequence of oxidation of bile acid hydroxyl groups, particularly the 7-hydroxyl group, by colonic bacteria. However, keto-bile acids are rapidly reduced by the liver to the corresponding α or β-hydroxy bile acids. For example, the corresponding keto bile acid of a CDCA is 7-keto lithocholic acid and one of its reduction products with the corresponding β-hydroxy bile acid is ursodeoxycholic acid (3α-7β-dihydroxy-5β-cholanic acid) ("UDCA"), a tertiary bile acid.

UDCA, a major component of bear bile, has been used for the treatment of and the protection against many types of liver disease for a little over 70 years as a major pharmaceutical agent. Its medicinal uses include the dissolution of radiolucent gall stones, the treatment of biliary dyspepsias, primarily biliary cirrhosis, primary sclerosing choplangitis, chronic active hepatitis and hepatitis C. In other mammalian species, bile acids containing a 6β-hydroxyl group, which are found in rats and mice, are known as muricholic acid; 6α-hydroxy bile acids produced by swine are termed hyocholic acid and hyodeoxycholic acids. 23-hydroxy bile acids of aquatic mammals are known as phocecholic and phocedeoxycholic acids.

Under normal circumstances, more than 99 percent of naturally occurring bile salts secreted into human bile are conjugated. Conjugates are bile acids in which a second organic substituent (e.g. glycine, taurine, glucuronate, sulfate or, rarely, other substituents) is attached to the side chain carboxylic acid or to one of the ring hydroxyl groups via an ester, ether, or amide linkage. Therefore, the ionization properties of conjugated bile acids with glycine or taurine are determined by the acidity of the glycine or taurine substituent.

Free, unconjugated, bile acid monomers have pKa values of approximately 5.0. However, pKa values of glycine conjugated bile acids are on average 3.9, and the pKa of taurine conjugate bile acids are less than 1.0. The effect of conjugation, therefore, is to reduce the pKa of a bile acid so that a large fraction is ionized at any given pH. Since the ionized salt form is more water soluble than the protonated acid form, conjugation enhances solubility at a low pH. Free bile acid salts precipitate from aqueous solution at pH 6.5 to 7. In contrast, precipitation of glycine conjugated bile acid occurs only at pH of less than 5. Taurine conjugated bile acids remain in aqueous solution under very strongly acidic conditions (lower than pH 1). However, in the gastric pH range, certain bile acids such as UDCA and CDCA are no longer soluble.

Conjugation of the side chain of a bile acid with glycine or taurine has little influence on the hydrophobic activity of fully ionized bile salts. More hydrophobic bile salts exhibit greater solubilizing capacity for phospholipid and cholesterol and are consequently better detergents. More hydrophobic bile salts are also more injurious to various membranes, both in vivo and in vitro.

Natural bile salt pools invariably contain multiple bile acid salts. Mixtures of two or more bile salts of differing hydrophobic activity may behave as a single bile salt of an intermediate hydrophobic activity. As a result, detergent properties and the toxicity of mixtures of two bile acids of differing hydrophobic activity often are intermediate between the individual components. Biologic functions and biologic properties of bile acids resulting from their amphiphillic properties are as follows:

I. Bile acid synthesis from cholesterol is one of the two principal pathways for the elimination of cholesterol from the body.

II. Bile flow is generated by the flux of bile salts passing through the liver. Bile formation represents an important pathway for solubilization and excretion of organic compounds, such as bilirubin, endogenous metabolites, such as emphipathic derivatives of steroid hormones; and a variety of drugs and other xenobiotics.

III. Secretion of bile salts into the bile is coupled with the secretion of two other biliary lipids, that is, phosphatidylcholine (lecithin) and cholesterol; the coupling of bile salt output with the lecithin and cholesterol output provides a major pathway for the elimination of hepatic cholesterol.

IV. Bile salts, along with lecithin, solubilize cholesterol in bile in the form of mixed micelles and vesicles. Bile salt deficiency, and consequently reduced cholesterol solubility in bile, may play a role in the pathogenesis of cholesterol gallstones.

V. Bile acids are thought to be a factor in the regulation of cholesterol synthesis. At present, it is not certain whether they regulate the cholesterol synthesis by acting directly on the hydroxymethylglutaryl-coenzyme A (HMG-CoA) reductase or indirectly by modulating the cholesterol absorption in the intestine.

VI. Bile salts in the enterohepatic circulation are thought to regulate the bile acid synthesis by suppressing or derepressing the activity of cholesterol 7-hydroxylase, which is the rate-limiting enzyme in the bile acid biosynthesis pathway.

VII. Bile acids may play a role in the regulation of hepatic lipoprotein receptors (apo B.E.) and consequently may modulate the rate of uptake of lipoprotein cholesterol by the liver.

VIII. In the intestines, bile salts in the form of mixed micelles participate in the intraluminal solubilization, transport, and absorption of cholesterol, fat-soluble vitamins, and other lipids.

IX. Bile salts may be involved in the transport of calcium and iron from the intestinal lumen to the brush border.

Recent drug delivery research concerning the characteristics and biofunctions of naturally occurring bile acid as an adjuvant and/or a carrier has focused on the derivatives and analogs of bile acids and bile acids themselves as novel drug delivery systems for delivery to the intestinal tract and the liver. These systems exploit the active transport mechanism to deliver aimed drug molecules to the specific target tissue by oral or cystic administration. Thus, if bile acids or bile acid derivatives are rapidly and efficiently absorbed in the liver and, consequently, undergo enterohepatic cycling, many potential therapeutic applications are foreseen including the following:

improvement of the oral absorption of an intrinsically, biologically active, but poorly absorbed hydrophillic and hydrophobic drug; liver site-directed delivery of a drug to bring about high therapeutic concentrations in the diseased liver with the minimization of general toxic reactions elsewhere in the body; and gallbladder-site delivery systems of cholecystographic agents and cholesterol gallstone dissolution accelerators. As an example, in 1985, Drs. Gordon & Moses et al. demonstrated that therapeutically useful amount of insulin are absorbed by the nasal mucosa of human beings when administered as a nasal spray with common bile salts such as DCA, UDCA, CDCA, CA, TUDCA, TCDCA, etc. See Moses, Alan C., et al., *Diabetes* vol. 32 (November 1983) 1040–1047; Gordon, G. S., et al., *Proc. Nat'l Acad. Sci. USA*, vol. 82 (November 1985) 7419–7423. In their experiment, bile acids produced marked elevations in serum insulin concentration, and about 50 percent decreases in blood glucose concentrations. However, this revolutionary nasal spray solution dosage form with bile acids (salts) as a adjuvant could not be developed further and commercialized, because the nasal spray solution must be prepared immediately prior to use due to the precipitation of bile acid salt and the instability of insulin at pH levels between 7.4 and 7.8. Moreover, as indicated in this disclosure, ursodeoxycholic acid as an adjuvant could not be used because of its insolubility at pH between 7.4 and 7.8.

The pH of the commercial insulin injection solutions are between 2.5 and 3.5 for acidified dosage forms and is between 7.00 and 7.4 for neutral dosage forms. Therefore, the safe and efficient preparations of any solution dosage forms of insulin with bile acid (salt) are not commercially available at this time, because of physically chemically incompatible characteristics of bile acids salts insolubility and the stability of insulin in acidic and neutral pH.

Heparin, a most potent anticoagulant, is widely used in the treatment of and in the prevention of thromboembolism. However, heparin treatment is usually limited to hospitalized patients since this drug is given only by injection. Alternate routes which have been attempted are an intrapulmonary spray, suppositories, and enema. According to numerous publications, for heparin absorption through the gastrointestinal mucosa to be facilitated, the preparations should be in acidic condition. According to Dr. Ziv, Dr. Eldor et al., heparin was absorbed through the rectal mucosa of rodents and primates only when administered in solutions containing sodium cholate or sodium deoxycholate. See Ziy E. et al., *Biochemical Pharmacology*, vol. 32, No. 5, pp. 773–776 (1983). Unfortunately, heparin is only stable in acidic conditions. Bile acids are particularly not soluble in acidic conditions. Therefore, due to their incompatible characteristics, the commercial dosage forms which heparin can be absorbed through the gastrointestinal mucosa with bile acids (salts) are not available at this time.

Drug delivery systems involving bile acids can provide liver-specific drug targeting which is of major interest for drug development since standard pharmacological approaches to liver diseases have been frustrated by the inadequate delivery of active agents into liver cells as well as non specific toxicity towards other organs. For example, the liver-specific delivery of a drug is necessary for inhibitors of collagen synthesis for the treatment for liver fibrosis in order to avoid unspecific and undesired side-effects in extrrhepatic tissues. Furthermore, for the treatment of cancer of the biliary system, high drug levels must be achieved in the liver and the biliary system, whereas in extrahepatic tissues low drug concentrations are desired to minimize the cytoxicity of the cytostatics to normal non-tumor cells. Dr. Kramer, Dr. Wess et al. demonstrate that hybrid molecules formed by covalent linkages of a drug to a modified bile acid molecule are recognized by the Na+-dependent bile acid uptake systems in the liver and the ileum. See U.S. Pat. No. 5,641,767. Even if bile acid salts and their derivatives act as shuttles for specific delivery of a drug to the liver, as already mentioned above, there are enormous risks to the development of the derivatives of bile acids or bile acid salts as carriers because new derivatives of bile acids or bile acid salts formed by covalent linkages of a drug to bile acid must be tested for its pharmacology, toxicity and clinical effectiveness. Thus, the development of preparations in which a drug can be absorbed with bile acids or bile acid salts from the places which contain the excessive bile acids in the intestine is far easier and far more valuable than the development of the new bile acid derivatives because less testing is required.

In spite of the extremely valuable therapeutic activities and the long historic medical uses of bile acids as therapeutically active agents and as carriers and/or adjuvants based on the already mentioned biological properties and functions of bile acids, the commercial administration of bile acids are limited to the pharmaceutical formulations with a solid form of bile acid which are in tablet, capsule and suspension because of its insolubility to aqueous media at pH from approximately 1 to 8, and its extremely bitter taste and equally bitter after-taste which lasts several hours. Note that ursodeoxycholic acid, chenodeoxycholic acid, and lithocholic acid are practically insoluble in water; that deoxycholic acid and cholic acid have solubilities of 0.24 g/l, and 0.2 g/l, respectively, and that tauroursodeoxycholic acid, taurochenodeoxycholic acid, and taurocholic acid are insoluble in hydrochloric acid solution. The few aqueous dosage forms that are available are unstable, and have very limited uses because of pH control and maintenance problems. Moreover, some commercial pharmaceutical dosage forms of bile acids have been shown to have scant bioavailability as described in *European Journal of Clinical Investigation* (1985) 15, 171–178. Bile acid, especially ursodeoxycholic acid is poorly soluble in the gastro-duodeno jejunal contents of fasted subjects. From 21% to 50% of the ingested doses were recovered in solid form because of the unpredictable variations in the very slow progressive solubilization of solid ursodeoxycholic acid in the gastrointestinal track. Bile acids, particularly ursodeoxycholic acid, deoxycholic acid, chenodeoxycholic acid, cholic acid, hyodeoxycholic acid, 7-keto lithocholic acid, tauroursodeoxycholic acid, and taurochenodeoxycholic acid among others, are especially insoluble in the gastric juices and in aqueous hydrochloric acid solution. However, the solubility of bile acids increase with the increase of the pH in the intestine very slowly and incompletely, and eventually the bile acids become soluble at pH between 8 and 9.5.

To overcome this slow and inefficient absorption process in the intestine due to the incomplete and slow solubilization of bile acids, many newly developed pharmaceutical formulations have been prepared, such as delayed release dosage forms with water soluble solid bile acids which are often strongly alkaline. These newly developed pharmaceutical dosage forms are enterosoluble-gastro resistant. These enterosoluble-gastroresistant dosage forms remain intact in gastric juices in the stomach, but are dissolved and release the strongly alkaline solid bile salts of the formulations at the targeted area, within a limited time once they reach the small intestine.

These types of dosage forms, of course, showed better bioavailability than presently commercialized dosage forms as described in U.S. Pat. No. 5,380,533. However, it is extremely difficult and very costly to prepare the precise delayed release dosage forms which can release therapeutically active components by disintegration, dissolution and diffusion at the desired area within a limited time. According to U.S. Pat. No. 5,302,398, the absorption test of the gastroresistant enterosoluble dosage forms of bile acids, particularly ursodeoxycholic acid in man show that its absorption increases a value of about 40 percent in comparison with administering the same amount in current commercial dosage forms. Its maximum hematic concentrations are on average three times higher, and are reached faster than with the commercial formulations. Any dosage forms of bile acid formula must be capable of releasing bile acids in a known and consistent manner following administration to the patient. Both the rate and the extent of release are important, and should be reproducible. Ideally, the extent of release should approach 100 percent, while the rate of release should reflect the desired properties of the dosage form.

It is a well-known fact that solution dosage forms of drugs show significantly improved rates and extents of absorption, compared to the same drug formulated as a tablet, capsule, or suspension. This is because solution dosage forms are chemically and physically homogeneous solutions of two or more substances. Moreover, the specially designed solution dosage forms which can maintain the solution systems without breaking down under any pH conditions are ready to be diffused in the desired area for immediate and complete absorption, whereas tablets, capsules or delayed release formulations must invariably undergo disintegration, dissolution and diffusion at the desired area within a limited time. Once again, unpredictable variations in the extent and rate of release of bile acids by the disintegration, dissolution and diffusion of delayed or immediate release dosage forms having pH-dependent instability result in the slow and inefficient absorption, and reduced bioavailability in comparison with the solution dosage forms which can reach the targeted area throughout the gastrointestinal track without any break-down of the solution system caused by the pH of the environment in the stomach and intestines. When the therapeutically active ingredients in aqueous solution forms are not precipitated as solid by acidic gastric juices in the stomach and by the various alkaline pH levels of the intestine, the formulation overcomes as a natural consequence, the scarce bioavailability resulted by the unexpected, undesirable results for the extent and the rate of release by disintegration, dissolution and/or diffusion should be overcome.

SUMMARY OF THE INVENTION

In one aspect of the invention a composition is provided which comprises a bile acid, its derivative, its salt, or its conjugate with an amine, water, and a sufficient quantity of high molecular weight aqueous soluble starch conversion product such that the bile acid and the starch conversion product remain in solution at any pH within a selected pH range.

In another aspect of the invention a pharmaceutical composition is provided which comprises a bile acid, its salt, or its conjugate with an amine, water, a pharmaceutical compound in a pharmaceutically appropriate amount, and a sufficient quantity of a high molecular weight aqueous soluble starch conversion product such that the bile acid, the pharmaceutical compound, and the starch conversion product remain in solution at any pH level within a selected pH range.

BRIEF DESCRIPTION OF THE DRAWINGS

Table I-1: Results of the test of the stability of the formulations of CA, 7-ketolithocholic acid, CDCA and DCA in solution with maltodextrin at pH 7 and 50° C. over time according to Examples I and II. The concentrations of the bile acids were measured by HPLC and the concentration of the bile acid as a percentage of its concentration on day 0 is reported in the column labeled percentage.

Table I-2: Results, presented, as in Table I-1, of the tests of stability of CA, 7-ketolithocholic acid, CDCA and DCA in solution with maltodextrin at pH 10 and 50° C. over time according to Examples I and II.

Figure 1:
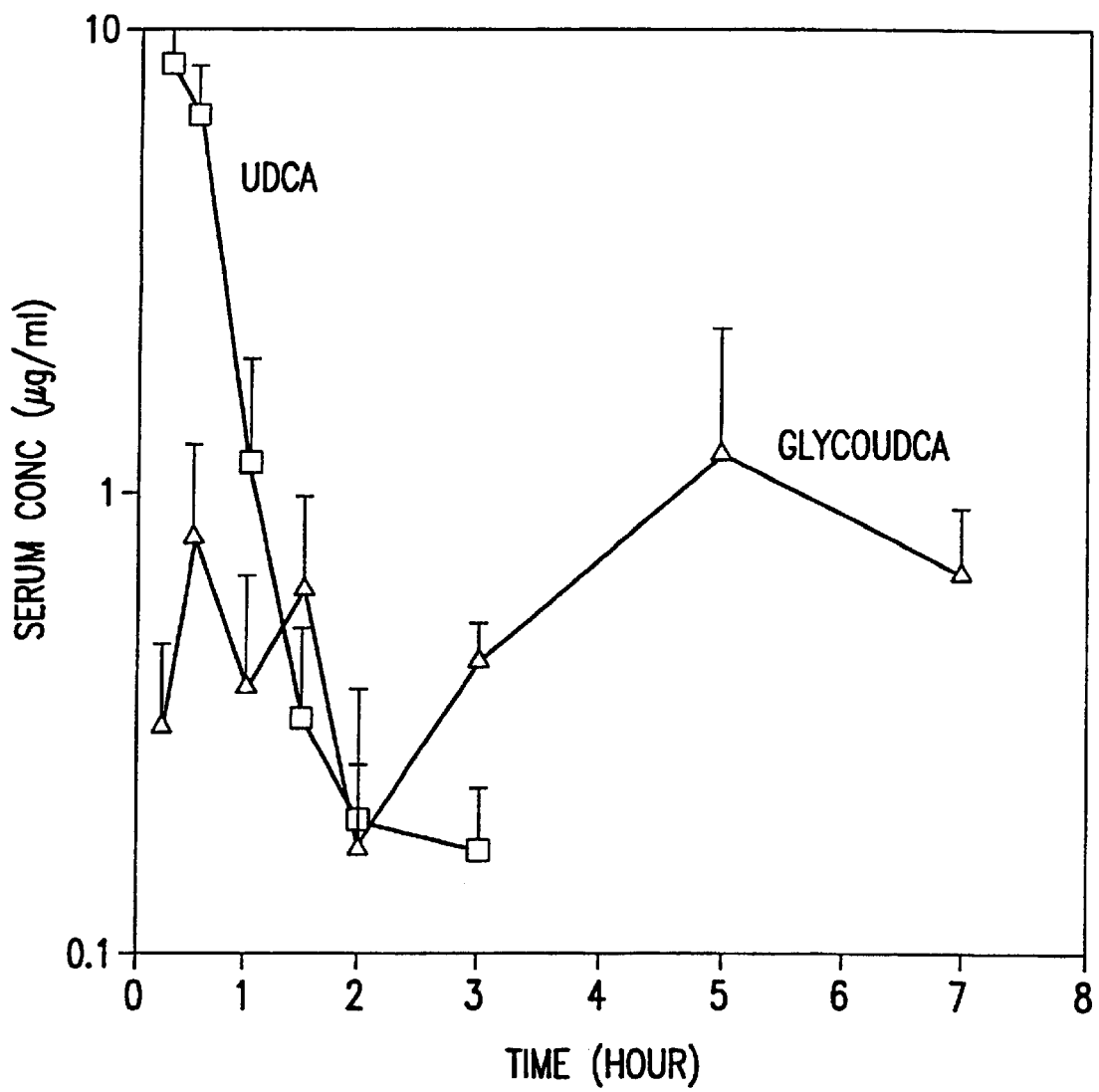
Figure 2:
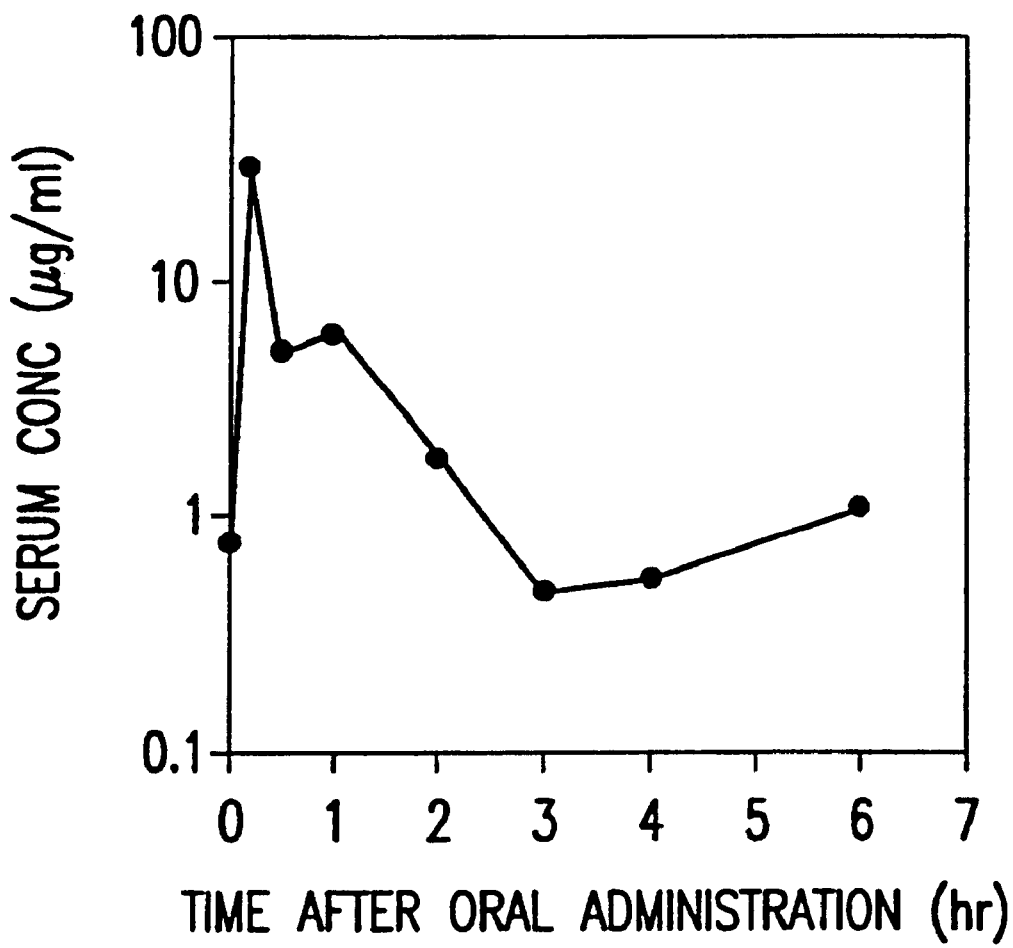

Table II: Results, presented as in Table I-1, of the tests of stability of CA, 7-ketolithocholic acid, CDCA and DCA in solution with maltodextrin at pH 1 and 50° C. over time according to Examples I and II.

Table III-1: Results, presented as in Table I-1, of the tests of stability of UDCA containing formulations prepared with amino acids according to Example IV at pH 1 and 50° C. over time.

Table III-2: Results, presented as in Table I-1, of the tests of stability of UDCA containing formulations prepared with amino acids according to Example IV at pH 3 and 50° C. over time.

Table III-3: Results, presented as in Table I-1, of the tests of stability of UDCA containing formulations prepared with amino acids according to Example IV at pH 5 and 50° C. over time.

Table III-4: Results, presented as in Table I-1, of the tests of stability of UDCA containing formulations prepared with amino acids according to Example IV at pH 7 and 50° C. over time.

Table III-5: Results, presented as in Table I-1, of the tests of stability of UDCA containing formulations prepared with amino acids according to Example IV at pH 9 and 50° C. over time.

Table III-6: Results, presented as in Table I-1, of the tests of stability of UDCA containing formulations prepared with amino acids according to Example IV at pH 10 and 50° C. over time.

Table IV: Plasma concentration of UDCA and GUDCA measured in 3 men over time following on oral administration of the UCOA and GUDCA containing formulations according to Example VI and comparison of results against results of others employing different pharmaceutical formulations of UDCA.

Drawing I-1: Graph of blood serum—concentration of UDCA (squares) and GUDCA (triangles) versus time following administration of dosage formulations according to Examples II and VI and Table IV.

Drawing II: Graph of blood serum concentration of UDCA versus time following administration of dosage formulations of the bile acid according to Examples III and VI and Table IV.

DETAILED DESCRIPTION OF THE INVENTION

The invention is practiced by preparing in aqueous solution a composition comprising one or more soluble bile acids, aqueous soluble bile acid derivatives, bile acid salts, or bile acid conjugated with an amine, (collectively "bile acid"), water and one or more high molecular weight aqueous soluble starch conversion products in an amount sufficient to produce a solution which does not form a precipitate at any pH level within the desired pH range preferably not precipitating between pH 1 and pH 10, more preferably between pH 1 and pH 14, and most preferably at all pH values obtainable in an aqueous system. Consequently in an embodiment of this invention, the bile acid remains dissolved under acidic conditions as a free bile acid in spite of the general insolubility of bile acids under acidic conditions. The composition may be used as a pharmaceutical formulation which remains in solution without precipitation at prevailing pH levels in the mouth, stomach and the intestines. The composition may contain a bile acid or its salt which itself has pharmaceutical effectiveness or the formulation may act as a carrier, an adjuvant, or enhancer for the solubility of a pharmaceutical material which remains dissolved in the composition of the invention across the desired pH range It is an advantage of this invention that the formulation of aqueous solution systems, in which a bile acid, its derivative, or its salt, and a high molecular weight aqueous soluble starch conversion product are dissolved remain intact and in solution without precipitation at any pH environment from acidic to alkaline. These aqueous solution systems of bile acid or bile acid salt and high molecular weight aqueous soluble starch conversion product do not produce any precipitation or particles, and do not demonstrate any changes in physical appearance such as changes in clarity, color or odor following the addition of strong acids or alkali and several months observation under the accelerated conditions of storage at 50° C. These aqueous solution systems of bile acid, bile acid salt, its conjugate with amines, or its analog in the formulation of the invention for oral administration in this invention reach the intestine through the gastrointestinal track without precipitation of bile acids as solids by exposure to acidic gastric juices and alkaline juices of the intestine. These dissolved bile acid formulations demonstrating intact solution systems in the intestine can thus be effectively and completely absorbed and, consequently, undergo enterohepatic cycling. Also, it should be emphasized that in these aqueous solution systems of bile acid or bile acid salt and high molecular weight aqueous soluble starch conversion products, a carboxylic acid of the side chain of certain bile acids can be protonated (non-ionized) or ionized or simple carboxylic acid depending on pH conditions without either precipitation or changes in physical appearance.

Because this phenomenon of solubility across a wide pH range greatly effects the hydrophobicity and the hydrophillicity of bile acids in these aqueous solution systems, they provide excellent advantages for controlling the toxicity, absorption, and amphiphilicity of bile acids. Bile acids are dissolved in these aqueous solution systems as a therapeutically active agent, as an adjuvant of a drug as a carrier of drug, or as an enhancer of drug solubility. These aqueous solution systems are prepared for oral consumption, enemas, mouthwashes, gargles, nasal preparations, otic preparations, injections, douches, topical skin preparations, and cosmetic preparations which have a desired pH without the disadvantage of precipitation or deterioration in physical appearance after long periods of time. Bile acids used in this invention include, but are not limited to ursodeoxycholic acid, chenodeoxycholic acid, cholic acid, hyodeoxycholic acid, deoxycholic acid, 7-oxolithocholic acid, lithocholic acid, iodedeoxycholic acid, iocholic acid, tauroursodeoxycholic acid, taurochenodeoxycholic acid, taurodeoxycholic acid, taurolithocholic acid, glycoursodeoxycholic acid, taurocholic acid, glycocholic acid, and their derivatives at a hydroxyl or carboxylic acid group on the steroid nucleus.

Soluble bile acids are any type of aqueous soluble bile acids. A bile acid salt is any aqueous soluble salt of a bile acid. The soluble bile acid derivatives of this invention are those derivatives which are as soluble or more soluble in aqueous solution than is the corresponding underivatized bile acid. Bile acid derivatives include, but are not limited to derivatives formed at the hydroxyl and carboxylic acid groups of the bile acid with other functional groups including but not limited to halogens and amino groups. Aqueous dissolved salts of bile acids may be formed by the reaction of bile acids described above and an amine including but not limited to aliphatic free amines such as trientine, diethylene triamine, tetraethylene pentamine, and basic aminoacids such as arginine, lysine, ornithine, and ammonia, and aminosugars such as D-glucamine, N-alkylglucamines, and quantemary ammonium derivatives such as choline, heterocyclic amines such as piperazine, N-alkylpiperazine, peperidine, N-alkylpiperidine, morpholine, N-alkyhnorphline, pyrrolidine, triethanolamine, and trimethanolamine. According to the invention, aqueous soluble metal salts of bile acids and aqueous soluble O-sulfonated bile acids are also included as soluble bile acid salts.

For purposes of the invention, high molecular weight aqueous soluble starch conversion products which can be obtained from the partial or incomplete hydrolysis of starch under various pH conditions are included but not limited maltodextrin, dextrin, dextran, liquid glucose, and soluble starch, preferably maltodextrin. The amount of high molecular weight aqueous soluble starch conversion product used in the invention is at least the amount needed to render the chosen bile acid salt soluble in the concentration desired and in the pH range desired. Preferably, the minimal required quantities of maltodextrin as one of starch conversion products which prevent the precipitation of bile acids from the aqueous solution dosage forms of the invention, is approximately 5 g for every 0.2 g of ursodeoxycholic acid, approximately 25 g for every 1 g of ursodeoxycholic acid, and approximately 50 g for every 2 g of ursodeoxycholic acid in 100 ml of water. In the case of liquid glucose (commercial light corn syrup) the preferable minimal quantities of liquid glucose is approximately 80 g for every 500 mg ursodeoxycholic acid in 100 ml water, and approximately 80 g for every 500 mg ursodeoxycholic acid in 200 ml water. The minimal required quantity of high molecular weight aqueous soluble starch conversion products is primarily determined by the absolute quantity of bile acids in the solution formulation rather than the concentration. Further, the preferable minimal required quantities of maltodextrin are approximately 30 g for every 200 mg of chenodeoxycholic acid, approximately 12 g for every 200 mg of 7-ketolithocholic acid, approximately 10 g for every 200 mg of cholic acid and approximately 50 g for every 200 mg of deoxycholic acid.

The selected pH range for which the formulation will not precipitate its bile acid, starch conversion product, or its pharmaceutical compound may be any range of pH levels obtainable with an aqueous system, preferably between pH 1 and pH 14, more preferably between pH 1 and pH 10, more preferably any subset of the range of pH levels obtainable in an aqueous system sufficient for the pharmaceutical formulation to remain in solution from preparation, to administration to absorption is the body, according to the method of administration.

Additional pharmaceutical compounds which may be included in the formulation are any compounds which remain soluble when added to the formulation. With an additional pharmaceutical compound in the formulation, a bile acid in solution may act as an adjuvant, carrier, or enhancer for the solubility of certain therapeutically active agents, including, but not limited to, insulin (pH 7.4–7.8), heparin (pH 5–7.5), calcitonin, ampicillin, amantadine, rimantadine, sildenafil, neomycin sulfate (pH 5–7.5), apomorphine, yohimbin, trazodone, ribavirin, paclitaxel and its derivatives, retinol, and tretinoin, which are soluble and stable in acid and/or alkali and can be added as needed into these aqueous solution dosage forms of certain concentrations of bile acids in this invention. Certain therapeutically active agents, including, but not limited to, metformin HCl (pH 5–7), ranitidine HCl, cimetidine, lamivudine, cetrizine 2HCl (pH 4–5), mantadine, rimantadine, sildenafil, apomorphine, yohimbine, trazodone, ribavirin and examethasone, hydrocortisone, prednisolone, triamcinolone, cortisone, niacin, taurine, vitamins, naturally occurring amino acids, and catechin and its derivatives, which are soluble and stable in acid and/or alkali can be added as needed into these aqueous solution dosage formulations containing ursodeoxycholic acid in this invention.

EXAMPLES

The stability of dosage formulations of the invention were evaluated by measuring the concentration of the relevant bile acid over time in preparations comprising soluble bile acid, a high molecular weight aqueous soluble starch conversion product, and water at various pH and temperature levels.

The stability tests were conducted on three different aqueous solution systems:

1. A bile acid and a high molecular aqueous soluble starch conversion product were combined in aqueous solution according to Example I, with results as shown in Table I-1.
2. Mixed bile acids and high molecular aqueous soluble starch conversion products were combined in aqueous solution according to Example II, with results as shown in Tables I-1, I2, II.
3. Bile acids, high molecular aqueous soluble starch conversion products and branched chained amino acids (e.g. leucine, isoleucine, valine, or other amino acid with a branched side chain) were combined in aqueous solution according to Example IV, with results as shown in Tables III-1, III-2, III-3, III-4, III-5, & III-6.

The stability tests were performed with HPLC and microscope light at various pH conditions under the normal and accelerated conditions. All of these stability test results were satisfactory in that the concentration of bile acid as measured by HPLC did not change appreciably over time at various pH levels. Thus the formulations of the examples are suitable for preparing a commercial liquid dosage form. Particularly, all solution formulations which contained bile acid showed excellent results in the stability tests with no precipitation and no physical appearance changes for over 2 years.

Moreover, the solution stability tests were conducted on the aqueous solution dosage forms comprising the mixture of aqueous soluble UDCA, branched chained amino acid (leucine, isoleucine, valine) and maltodextrin according to example IV as a typical example of the solution dosage forms in which bile acid as a therapeutically active agent, as an adjuvant or carrier, pharmaceutically active agent, or enhancer of solubility, and high molecular weight aqueous soluble starch conversion products are dissolved. According to the test results, there is no discoloration, no clarity changes, and no precipitation. Furthermore, there are no detectable impurities from the deterioration of UDCA or branched chained amino acids when examined by HPLC at various pH conditions such as pH 1, 3, 5, 7, 9, and 10 under the accelerated conditions or incubation at (50° C.).

The aqueous solution dosage forms according to this invention did not change either physically or chemically at various pH conditions under the accelerated conditions despite the addition of therapeutically and chemically active agents that are table and soluble in hydrochloric acid solution. Therefore, these aqueous solution systems are extremely valuable pharmaceutical dosage forms for the therapeutically active bile acids preparations, and/or the drug (pharmaceutical compound) delivery preparations in which bile acids play roles as the adjuvant of drug, the carrier of drug, or the enhancer of solubility of a drug by micelle formation at various pH conditions without the stability problems, including precipitation in acidic conditions.

For the solution stability test for each bile acid, HPLC was used to measure the concentration of the relevant soluble bile acid under the following conditions: the elution solvent of $0.02MKH_2PO_4$: acetonitrile in a ratio of 55:45, with a pH of 3.01, the flow rate was 0.8 ml/min., the injection volume was 20 μl, wave length for detection was 195 nm. In the tables, the concentration of the indicated bile acid salt for each of the three numbered trials and the average thereof is reported on each line. The percentage indicates the relative concentration of the bile acid salt after incubation for a certain amount of time in comparison with the initial concentration.

Example I

The following solution dosage forms were prepared and they did not show any precipitation at any pH.

| | |
|---|---|
| Soluble bile acid | 200 mg (as free acid) |
| Minimal quantity of maltodextrin | (for CDCA: approx. 30 g of maltodextrin; for UDCA: approx. 5 g; for 7-ketolithocholic acid: approx. 12 g; for cholic acid: approx. 10 g; |

| | |
|---|---|
| | for deoxycholic acid: approx. 50 g; for hyodeoxycholic acid: approx 3.5 g) |
| Purified water | 100 ml |

1001 ml of the aqueous solution in which one of the above bile acids is dissolved was prepared. Into the resulting clear solution, maltodextrin, a high molecular weight aqueous soluble starch conversion product, was added with agitation at room temperature.

The minimal quantity of liquid glucose needed instead of maltodextrin was approximately: for 0.1 g UDCA, 76 ml; for 0.1 g CDCA, 80 ml; for 1.0 g cholic acid, 10 ml; for 0.1 g 7-ketolithocholic acid, 80 ml; for 0.1 g hyodeoxycholic acid, 70 ml; for 0.1 g deoxycholic acid, 500 ml.

Based on these formulas, the aqueous solution dosage forms of various concentrations of certain bile acids (or salts) with its corresponding minimal quantity or more of high molecular weight aqueous soluble starch conversion products (for example; maltodextrin, liquid glucose, dextran, dextrin, and soluble starch) were prepared.

Example II

The following solution dosage forms were prepared and they did not show any precipitation at any pH.

| | |
|---|---|
| Soluble cholic acid | 200 mg (as free acid), |
| Soluble 7-ketolithocholic acid | 200 mg (as free acid), |
| Soluble chenodeoxycholic acid | 200 mg (as free acid), |
| Minimal quantity of maltodextrin | 40 g, and |
| Purified water | 100 ml |

100 ml of the aqueous solution in which soluble cholic acid, soluble 7-ketolithocholic acid, soluble chenodeoxycholic acid, chohc acid are dissolved, was prepared. Into the resulting clear solution, maltodextrin was added with agitating at room temperature.

Using this formulation, the stability test for the aqueous solution of the mixture of various bile acids which can control the hydrophillicity or hydrophobicity was conducted.

Example III

The following solution dosage forms were prepared and they did not show any precipitation at any pH.

| | |
|---|---|
| Soluble UDCA | 200 mg (50 mg–2000 mg as free base) |
| Minimal quantity of maltodextrin | approx. 5 g (approx. 1.25 g–50 g) |
| Preservatives | q.s. |
| Flavoring agent | q.s. |
| Sweetener | q.s. |
| Purified water | 100 ml |

80 ml of the aqueous solution in which soluble UDCA is dissolved was prepared, and then, maltodextrin as one of high molecular weight aqueous soluble starch conversion products was added into the clear solution with agitating at room temperature. Into the resulting clear solution, sweetener, preservatives and flavoring agents were added in quantities suitable for a pharmaceutical formulation. Purified water is added to make total 100 ml.

In these formulas, the aqueous solution dosage forms of various concentrations of ursodeoxycholic acid (or its salts) with its corresponding minimal quantity or more of high molecular weight aqueous soluble starch conversion products (for example, maltodextrin, liquid glucose, dextrin, dextran, or soluble starch) were prepared.

The minimal corresponding quantity of maltodextrin for the various amounts of UDCA in this solution preparation are as follows: for 0.2 g of UDCA: approx. 5 g of maltodextrin, for 0.4 g of UDCA: approx. 10 g of maltodextrin, for 1 g of UDCA: approx. 25 g of maltodextrin, for 2 g of UDCA: approx. 50 g of maltodextrin. The minimal corresponding quantity of liquid glucose for the various amount of UDCA are as follows: for 0.2 g of UDCA: approx. 16 g of liquid glucose, for 0.5 g of UDCA: approx. 80 g of liquid glucose. The minimal corresponding quantity of dextran for 500 mg of UDCA is approximately 52–55 g of dextran.

Example IV

The following solution dosage forms were prepared and they did not show any precipitation at any pH level within the selected, desired range of pH values.

| | |
|---|---|
| Soluble UDCA | 0.2 g (0.05 g–2 g as free acid) |
| Maltodextrin as one of the high molecular weight aqueous soluble starch conversion products | 5 g (1.25 g–50 g) |
| Branched chained amino acid (leucine, isoleucine, valine) | 15 g (5 g–15 g as free base) |
| Sweetener | q.s. |
| Flavoring agent | q.s |
| Purified water to | 100 ml |

85 ml of the aqueous solution in which soluble UDCA is dissolved was prepared, and then maltodextrin, as one of the high molecular weight aqueous soluble starch conversion products, was added into the clear solution. Into the resulting clear solution, branched aminoacids were added with adjusting the pH(4–7) with agitation and then sweetener, preservatives, and flavoring agent were added.

Based on these formulations, the aqueous solution dosage forms of various concentrations of ursodeoxycholic acid (or its salt) and its corresponding minimal quantity or more of high molecular weight aqueous soluble starch conversion products, such as, maltodext, liquid glucose dextrin, or dextran) with various quantities of branched aminoacid (total amount of leucine, isoleucine and valine) were prepared.

Example V

The following solution dosage form was prepared and the resulting solution did not form a precipitate at all pH levels within the selected, desired pH range. This formulation is based on the known analytical data for pharmaceutical use of bear bile.

| | |
|---|---|
| Tauro UDCA | 7 g |
| Tauro CDCA | 1 g |
| Glyco UDCA | 0.8 g |
| Glyco CDCA | 0.2 g |
| Soluble UDCA | 1 g (or 3 g as free form) |

High molecular weight aqueous soluble starch conversion product 250 g.

| | |
|---|---|
| Water | 2 l. |
| Sweetener | q.s. |
| Flavoring agent | q.s. |

Soluble UDCA is dissolved in water and then high molecular weight aqueous soluble starch conversion product and water are added. Into the resulting clear solution, Tauro UDCA, Tauro CDCA, Glyco UDCA, Glyco CDCA, Sweetener, and Flavoring agent were added.

Example VI

The aqueous solution dosage forms, according to this invention, containing 200 mg of ursodeoxycholic acid (UDCA), were prepared according to the method described in the above-described Example III and were administered to three healthy men having normal body weight after fasting. The hematic levels of UDCA and glyco UDCA were evaluated by means of well known chemical methods. After applying buffered serum to sep-pak column, methanol eluate was derivatized with phenacyl bromide at 80° C. for 45 minutes. These phenacyl bromide derivatives were dissolved in acetonitrile in preparation for HPLC. The experimental results of the absorption measured at certain times after dosage administration include the total absorption expressed as the area under the serum concentration-time curve (AUC: ug/ml×hours), the maximum hematic concentration (Cmax; ug/ml) that has been obtained, and the time (Tmax; hour) in which said maximum concentration has been obtained. These results are reported in Table IV, Drawing I-1 & II.

The experimental pharmacokinetic tests of the aqueous solution dosage forms according to this invention carried out on men show substantial improvement in AUC, Cmax and Tmax in comparison with the best results from any dosage forms known presently. The maximum hematic concentration (Cmax) in Table IV shows an average of 8.43±1.69 ug/ml which is at least two times higher than that reported for use of enteric coated Na salt of UDCA preparations and, four times higher than that obtained using regular UDCA tablet preparations. Moreover, the time of peak concentration (Tmax) which is related closely to the rate of absorption of UDCA from the aqueous solution dosage forms is 0.25 hours, at least three times faster than the fastest Tmax previously known.

TABLE I-1

| | Day | #1 | #2 | #3 | Average | Percentage |
|---|---|---|---|---|---|---|
| CA | 0 | 0.529 | 0.530 | 0.522 | 0.527 | 100.0 |
| | 4 | 0.460 | 0.524 | 0.524 | 0.502 | 95.4 |
| | 7 | 0.520 | 0.525 | 0.547 | 0.531 | 100.8 |
| | 20 | 0.516 | 0.576 | 0.535 | 0.542 | 103.0 |
| KLCA | 0 | 0.888 | 0.879 | 0.874 | 0.880 | 100.0 |
| | 4 | 0.871 | 0.887 | 0.888 | 0.882 | 100.2 |
| | 7 | 0.897 | 0.893 | 0.888 | 0.893 | 101.4 |
| | 20 | 0.893 | 0.909 | 0.894 | 0.899 | 102.1 |
| CDCA | 0 | 0.572 | 0.539 | 0.530 | 0.547 | 100.0 |
| | 4 | 0.540 | 0.552 | 0.576 | 0.556 | 101.6 |
| | 7 | 0.581 | 0.588 | 0.553 | 0.574 | 105.0 |
| | 20 | 0.565 | 0.608 | 0.560 | 0.578 | 105.7 |
| DCA | 0 | 0.499 | 0.491 | 0.489 | 0.493 | 100.0 |
| | 4 | 0.501 | 0.500 | 0.474 | 0.491 | 99.6 |
| | 7 | 0.488 | 0.487 | 0.484 | 0.486 | 98.6 |
| | 20 | 0.478 | 0.476 | 0.472 | 0.475 | 96.3 |

TABLE I-2

| | Day | #1 | #2 | #3 | Average | Percentage |
|---|---|---|---|---|---|---|
| CA | 0 | 0.534 | 0.524 | 0.490 | 0.516 | 100.0 |
| | 4 | 0.501 | 0.509 | 0.524 | 0.511 | 99.1 |
| | 7 | 0.552 | 0.518 | 0.533 | 0.534 | 103.6 |
| | 20 | 0.535 | 0.563 | 0.548 | 0.549 | 106.4 |
| KLCA | 0 | 0.879 | 0.874 | 0.857 | 0.870 | 100.0 |
| | 4 | 0.870 | 0.873 | 0.880 | 0.874 | 100.5 |
| | 7 | 0.893 | 0.876 | 0.882 | 0.884 | 101.5 |
| | 20 | 0.887 | 0.893 | 0.887 | 0.889 | 102.2 |
| CDCA | 0 | 0.541 | 0.532 | 0.495 | 0.522 | 100.0 |
| | 4 | 0.511 | 0.519 | 0.538 | 0.523 | 100.0 |
| | 7 | 0.564 | 0.527 | 0.540 | 0.544 | 104.1 |
| | 20 | 0.556 | 0.569 | 0.558 | 0.561 | 107.4 |
| DCA | 0 | 0.491 | 0.488 | 0.471 | 0.483 | 100.0 |
| | 4 | 0.493 | 0.487 | 0.472 | 0.484 | 100.2 |
| | 7 | 0.479 | 0.488 | 0.479 | 0.482 | 99.7 |
| | 20 | 0.468 | 0.478 | 0.479 | 0.475 | 98.3 |

TABLE II

| | Day | #1 | #2 | #3 | Average | Percentage |
|---|---|---|---|---|---|---|
| CA | 0 | 0.516 | 0.509 | 0.503 | 0.509 | 100.0 |
| | 4 | 0.453 | 0.453 | 0.466 | 0.457 | 89.8 |
| | 7 | 0.434 | 0.426 | 0.468 | 0.443 | 86.9 |
| | 20 | 0.207 | — | 0.206 | 0.207 | 40.6 |
| KLCA | 0 | 0.883 | 0.877 | 0.869 | 0.876 | 100.0 |
| | 4 | 0.870 | 0.866 | 0.847 | 0.861 | 98.3 |
| | 7 | 0.848 | 0.844 | 0.843 | 0.845 | 96.4 |
| | 20 | 0.661 | — | 0.651 | 0.656 | 74.9 |
| CDCA | 0 | 0.560 | 0.528 | 0.513 | 0.534 | 100.0 |
| | 4 | 0.488 | 0.510 | 0.519 | 0.506 | 94.7 |
| | 7 | 0.460 | 0.469 | 0.463 | 0.464 | 87.0 |
| | 20 | 0.169 | — | 0.154 | 0.161 | 30.2 |

TABLE III-1

| | Day | #1 | #2 | #3 | Average | Percentage |
|---|---|---|---|---|---|---|
| Ile | 0 | 0.261 | 0.236 | 0.249 | 0.248 | 100.0 |
| | 1 | 0.256 | 0.275 | 0.251 | 0.261 | 105.0 |
| | 2 | 0.268 | 0.263 | 0.251 | 0.260 | 104.9 |
| | 6 | 0.295 | 0.268 | 0.291 | 0.285 | 114.6 |
| | 7 | 0.249 | 0.254 | 0.267 | 0.257 | 103.4 |
| | 8 | 0.253 | 0.243 | 0.240 | 0.245 | 98.8 |
| | 9 | 0.263 | 0.268 | 0.263 | 0.265 | 106.6 |
| Leu | 0 | 0.485 | 0.428 | 0.470 | 0.461 | 100.0 |
| | 1 | 0.470 | 0.477 | 0.456 | 0.468 | 101.5 |
| | 2 | 0.485 | 0.481 | 0.460 | 0.475 | 103.1 |
| | 6 | 0.553 | 0.510 | 0.529 | 0.531 | 115.1 |
| | 7 | 0.478 | 0.473 | 0.513 | 0.488 | 105.8 |
| | 8 | 0.474 | 0.454 | 0.511 | 0.480 | 104.0 |
| | 9 | 0.483 | 0.485 | 0.476 | 0.481 | 104.4 |
| Val | 0 | 0.506 | 0.448 | 0.460 | 0.471 | 100.0 |
| | 1 | 0.438 | 0.458 | 0.471 | 0.456 | 96.7 |
| | 2 | 0.479 | 0.485 | 0.513 | 0.492 | 104.5 |
| | 6 | 0.505 | 0.536 | 0.549 | 0.530 | 112.4 |
| | 7 | 0.494 | 0.465 | 0.496 | 0.485 | 102.9 |
| | 8 | 0.488 | 0.491 | 0.459 | 0.479 | 101.7 |
| | 9 | 0.479 | 0.496 | 0.490 | 0.488 | 103.6 |
| Sol | 0 | 0.319 | 0.315 | 0.322 | 0.319 | 100.0 |
| | 1 | 0.332 | 0.344 | 0.351 | 0.342 | 107.4 |
| | 2 | 0.371 | 0.339 | 0.403 | 0.371 | 116.4 |
| | 6 | 0.396 | 0.409 | 0.411 | 0.405 | 127.2 |
| | 7 | 0.365 | 0.351 | 0.381 | 0.366 | 114.7 |
| | 8 | 0.409 | 0.365 | 0.331 | 0.368 | 115.6 |
| | 9 | 0.338 | 0.391 | 0.374 | 0.368 | 115.4 |
| UDCA | 0 | 0.388 | 0.387 | 0.389 | 0.388 | 100.0 |
| | 1 | 0.367 | 0.370 | 0.366 | 0.368 | 94.8 |
| | 2 | 0.374 | 0.388 | 0.388 | 0.383 | 98.9 |
| | 6 | 0.371 | 0.380 | 0.382 | 0.377 | 97.3 |
| | 7 | 0.378 | 0.376 | 0.379 | 0.378 | 97.4 |
| | 8 | 0.374 | 0.382 | 0.384 | 0.380 | 97.9 |
| | 9 | 0.370 | 0.367 | 0.370 | 0.369 | 95.1 |

TABLE III-2

|  | Day | #1 | #2 | #3 | Average | Percentage |
|---|---|---|---|---|---|---|
| Ile | 0 | 0.261 | 0.254 | 0.253 | 0.256 | 100.0 |
|  | 1 | 0.266 | 0.268 | 0.261 | 0.265 | 103.3 |
|  | 2 | 0.273 | 0.243 | 0.247 | 0.254 | 99.3 |
|  | 6 | 0.296 | 0.306 | 0.300 | 0.301 | 117.4 |
|  | 7 | 0.247 | 0.265 | 0.257 | 0.256 | 100.0 |
|  | 8 | 0.250 | 0.247 | 0.247 | 0.248 | 96.7 |
|  | 13 | 0.285 | 0.240 | 0.250 | 0.258 | 100.9 |
| Leu | 0 | 0.495 | 0.465 | 0.452 | 0.471 | 100.0 |
|  | 1 | 0.489 | 0.480 | 0.470 | 0.480 | 101.9 |
|  | 2 | 0.495 | 0.472 | 0.481 | 0.483 | 102.6 |
|  | 6 | 0.522 | 0.532 | 0.556 | 0.537 | 114.0 |
|  | 7 | 0.492 | 0.482 | 0.491 | 0.488 | 103.7 |
|  | 8 | 0.543 | 0.515 | 0.495 | 0.517 | 109.9 |
|  | 13 | 0.512 | 0.496 | 0.543 | 0.517 | 109.8 |
| Val | 0 | 0.485 | 0.491 | 0.498 | 0.491 | 100.0 |
|  | 1 | 0.467 | 0.481 | 0.446 | 0.465 | 94.6 |
|  | 2 | 0.510 | 0.493 | 0.527 | 0.510 | 103.8 |
|  | 6 | 0.527 | 0.491 | 0.553 | 0.524 | 106.6 |
|  | 7 | 0.485 | 0.481 | 0.468 | 0.478 | 97.3 |
|  | 8 | 0.490 | 0.491 | 0.544 | 0.508 | 103.5 |
|  | 13 | 0.519 | 0.498 | 0.517 | 0.511 | 104.1 |
| Sol | 0 | 0.343 | 0.355 | 0.370 | 0.356 | 100.0 |
|  | 1 | 0.340 | 0.350 | 0.316 | 0.335 | 94.2 |
|  | 2 | 0.383 | 0.371 | 0.400 | 0.385 | 108.0 |
|  | 6 | 0.378 | 0.341 | 0.416 | 0.378 | 106.3 |
|  | 7 | 0.355 | 0.381 | 0.315 | 0.350 | 98.4 |
|  | 8 | 0.343 | 0.350 | 0.395 | 0.363 | 101.9 |
|  | 13 | 0.377 | 0.382 | 0.423 | 0.394 | 110.7 |
| UDCA | 0 | 0.395 | 0.396 | 0.393 | 0.395 | 100.0 |
|  | 1 | 0.396 | 0.401 | 0.392 | 0.396 | 100.4 |
|  | 2 | 0.427 | 0.421 | 0.416 | 0.421 | 106.8 |
|  | 6 | 0.407 | 0.408 | 0.402 | 0.405 | 102.7 |
|  | 7 | 0.412 | 0.409 | 0.411 | 0.411 | 104.1 |
|  | 8 | 0.415 | 0.418 | 0.408 | 0.414 | 104.9 |
|  | 13 | 0.415 | 0.412 | 0.416 | 0.414 | 105.0 |

TABLE III-3

|  | Day | #1 | #2 | #3 | Average | Percentage |
|---|---|---|---|---|---|---|
| Ile | 0 | 0.285 | 0.258 | 0.295 | 0.279 | 100.0 |
|  | 3 | 0.280 | 0.275 | 0.275 | 0.277 | 99.0 |
|  | 6 | 0.285 | 0.273 | 0.270 | 0.276 | 98.7 |
|  | 10 | 0.274 | 0.276 | 0.276 | 0.275 | 98.4 |
|  | 13 | 0.273 | 0.287 | 0.278 | 0.279 | 100.0 |
|  | 17 | 0.278 | 0.276 | 0.270 | 0.275 | 98.3 |
|  | 20 | 0.261 | 0.275 | 0.261 | 0.266 | 95.0 |
|  | 24 | 0.267 | 0.274 | 0.292 | 0.277 | 99.3 |
| Leu | 0 | 0.495 | 0.467 | 0.535 | 0.499 | 100.0 |
|  | 3 | 0.510 | 0.495 | 0.494 | 0.500 | 100.1 |
|  | 6 | 0.489 | 0.479 | 0.484 | 0.484 | 97.0 |
|  | 10 | 0.486 | 0.490 | 0.499 | 0.492 | 98.5 |
|  | 13 | 0.492 | 0.509 | 0.508 | 0.503 | 100.8 |
|  | 17 | 0.514 | 0.508 | 0.504 | 0.509 | 100.9 |
|  | 20 | 0.499 | 0.500 | 0.499 | 0.499 | 101.1 |
|  | 24 | 0.488 | 0.509 | 0.528 | 0.508 | 101.9 |
| Val | 0 | 0.483 | 0.498 | 0.481 | 0.487 | 100.0 |
|  | 3 | 0.492 | 0.494 | 0.526 | 0.504 | 103.4 |
|  | 6 | 0.459 | 0.475 | 0.481 | 0.472 | 96.8 |
|  | 10 | 0.500 | 0.436 | 0.480 | 0.472 | 96.9 |
|  | 13 | 0.464 | 0.451 | 0.474 | 0.463 | 95.0 |
|  | 17 | 0.407 | 0.491 | 0.462 | 0.453 | 93.0 |
|  | 20 | 0.471 | 0.512 | 0.477 | 0.487 | 99.9 |
|  | 24 | 0.471 | 0.476 | 0.458 | 0.468 | 96.1 |
| Sol | 0 | 0.341 | 0.351 | 0.360 | 0.351 | 100.0 |
|  | 3 | 0.342 | 0.386 | 0.371 | 0.366 | 104.5 |
|  | 6 | 0.316 | 0.321 | 0.342 | 0.326 | 93.1 |
|  | 10 | 0.341 | 0.299 | 0.335 | 0.325 | 92.7 |
|  | 13 | 0.355 | 0.326 | 0.350 | 0.344 | 98.0 |
|  | 17 | 0.334 | 0.376 | 0.353 | 0.354 | 101.0 |
|  | 20 | 0.347 | 0.398 | 0.394 | 0.380 | 108.3 |
|  | 24 | 0.416 | 0.353 | 0.378 | 0.382 | 109.0 |
| UDCA | 0 | 0.407 | 0.404 | 0.404 | 0.405 | 100.0 |
|  | 3 | 0.409 | 0.402 | 0.403 | 0.405 | 99.9 |
|  | 6 | 0.410 | 0.403 | 0.409 | 0.407 | 100.6 |
|  | 10 | 0.404 | 0.405 | 0.407 | 0.405 | 100.1 |
|  | 13 | 0.408 | 0.403 | 0.395 | 0.402 | 99.3 |
|  | 17 | 0.411 | 0.402 | 0.404 | 0.406 | 100.2 |
|  | 20 | 0.405 | 0.394 | 0.396 | 0.398 | 98.4 |
|  | 24 | 0.399 | 0.408 | 0.406 | 0.404 | 99.9 |

TABLE III-4

|  | Day | #1 | #2 | #3 | Average | Percentage |
|---|---|---|---|---|---|---|
| Ile | 0 | 0.296 | 0.289 | 0.281 | 0.289 | 100.0 |
|  | 5 | 0.300 | 0.282 | 0.281 | 0.288 | 99.7 |
|  | 8 | 0.277 | 0.282 | 0.268 | 0.276 | 95.5 |
|  | 12 | 0.273 | 0.278 | 0.278 | 0.277 | 95.8 |
|  | 15 | 0.271 | 0.273 | 0.266 | 0.270 | 93.5 |
|  | 19 | 0.294 | 0.285 | 0.281 | 0.287 | 99.3 |
| Leu | 0 | 0.519 | 0.513 | 0.495 | 0.509 | 100.0 |
|  | 5 | 0.499 | 0.499 | 0.498 | 0.498 | 97.9 |
|  | 8 | 0.498 | 0.513 | 0.480 | 0.497 | 97.7 |
|  | 12 | 0.508 | 0.516 | 0.515 | 0.513 | 100.9 |
|  | 15 | 0.503 | 0.505 | 0.499 | 0.502 | 98.7 |
|  | 19 | 0.521 | 0.509 | 0.516 | 0.515 | 101.3 |
| Val | 0 | 0.483 | 0.530 | 0.525 | 0.513 | 100.0 |
|  | 5 | 0.502 | 0.447 | 0.499 | 0.483 | 94.1 |
|  | 8 | 0.488 | 0.498 | 0.493 | 0.493 | 96.2 |
|  | 12 | 0.490 | 0.469 | 0.443 | 0.467 | 91.2 |
|  | 15 | 0.492 | 0.541 | 0.442 | 0.492 | 95.9 |
|  | 19 | 0.458 | 0.500 | 0.482 | 0.480 | 93.6 |
| Sol | 0 | 0.333 | 0.352 | 0.363 | 0.349 | 100.0 |
|  | 5 | 0.344 | 0.309 | 0.349 | 0.334 | 95.6 |
|  | 8 | 0.334 | 0.379 | 0.377 | 0.363 | 104.0 |
|  | 12 | 0.345 | 0.344 | 0.317 | 0.335 | 96.0 |
|  | 15 | 0.286 | 0.406 | 0.321 | 0.338 | 96.7 |
|  | 19 | 0.338 | 0.416 | 0.351 | 0.368 | 105.4 |
| UDCA | 0 | 0.427 | 0.416 | 0.428 | 0.424 | 100.0 |
|  | 5 | 0.406 | 0.427 | 0.432 | 0.422 | 99.4 |
|  | 8 | 0.419 | 0.408 | 0.417 | 0.414 | 97.7 |
|  | 12 | 0.414 | 0.418 | 0.419 | 0.417 | 98.4 |
|  | 15 | 0.413 | 0.418 | 0.409 | 0.414 | 97.5 |
|  | 19 | 0.429 | 0.421 | 0.424 | 0.425 | 100.1 |

TABLE III-5

|  | Day | #1 | #2 | #3 | Average | Percentage |
|---|---|---|---|---|---|---|
| Ile | 0 | 0.291 | 0.286 | 0.282 | 0.286 | 100.0 |
|  | 3 | 0.266 | 0.273 | 0.282 | 0.273 | 95.6 |
|  | 6 | 0.277 | 0.274 | 0.272 | 0.274 | 95.9 |
|  | 10 | 0.243 | 0.245 | 0.295 | 0.261 | 91.2 |
|  | 13 | 0.246 | 0.269 | 0.236 | 0.250 | 87.4 |
|  | 17 | 0.275 | 0.280 | 0.245 | 0.267 | 93.1 |
| Leu | 0 | 0.509 | 0.513 | 0.511 | 0.511 | 100.0 |
|  | 3 | 0.485 | 0.487 | 0.492 | 0.488 | 95.5 |
|  | 6 | 0.495 | 0.496 | 0.492 | 0.494 | 96.8 |
|  | 10 | 0.470 | 0.467 | 0.528 | 0.488 | 95.6 |
|  | 13 | 0.461 | 0.491 | 0.450 | 0.467 | 91.5 |
|  | 17 | 0.468 | 0.516 | 0.500 | 0.495 | 96.9 |
| Val | 0 | 0.508 | 0.476 | 0.484 | 0.489 | 100.0 |
|  | 3 | 0.463 | 0.487 | 0.485 | 0.478 | 97.8 |
|  | 6 | 0.493 | 0.473 | 0.495 | 0.487 | 99.5 |
|  | 10 | 0.441 | 0.428 | 0.471 | 0.447 | 91.3 |
|  | 13 | 0.467 | 0.483 | 0.537 | 0.496 | 101.3 |
|  | 17 | 0.499 | 0.495 | 0.501 | 0.498 | 101.8 |
| Sol | 0 | 0.341 | 0.316 | 0.328 | 0.328 | 100.0 |
|  | 3 | 0.297 | 0.317 | 0.317 | 0.310 | 94.5 |
|  | 6 | 0.313 | 0.291 | 0.314 | 0.306 | 93.2 |
|  | 10 | 0.268 | 0.253 | 0.324 | 0.282 | 85.8 |
|  | 13 | 0.270 | 0.266 | 0.334 | 0.290 | 88.3 |
|  | 17 | 0.337 | 0.329 | 0.317 | 0.328 | 99.8 |

TABLE III-5-continued

| | Day | #1 | #2 | #3 | Average | Percentage |
|---|---|---|---|---|---|---|
| UDCA | 0 | 0.389 | 0.385 | 0.389 | 0.388 | 100.0 |
| | 3 | 0.405 | 0.400 | 0.394 | 0.400 | 103.2 |
| | 6 | 0.427 | 0.411 | 0.416 | 0.418 | 107.9 |
| | 10 | 0.420 | 0.418 | 0.450 | 0.429 | 110.8 |
| | 13 | 0.465 | 0.434 | 0.441 | 0.447 | 115.3 |
| | 17 | 0.454 | 0.457 | 0.413 | 0.441 | 113.9 |

TABLE III-6-continued

| | Day | #1 | #2 | #3 | Average | Percentage |
|---|---|---|---|---|---|---|
| Sol | 0 | 0.368 | 0.376 | 0.331 | 0.358 | 100.0 |
| | 2 | 0.284 | 0.257 | 0.266 | 0.269 | 75.1 |
| | 5 | 0.053 | 0.217 | 0.192 | 0.154 | 43.0 |
| | 7 | 0.042 | 0.026 | 0.156 | 0.075 | 20.8 |
| | 9 | 0.033 | 0.019 | 0.023 | 0.025 | 7.0 |
| UDCA | 0 | 0.416 | 0.402 | 0.406 | 0.408 | 100.0 |
| | 2 | 0.402 | 0.397 | 0.400 | 0.399 | 97.9 |
| | 5 | 0.425 | 0.413 | 0.423 | 0.420 | 103.0 |
| | 7 | 0.406 | 0.402 | 0.408 | 0.406 | 99.4 |
| | 9 | 0.424 | 0.426 | 0.421 | 0.423 | 103.8 |

TABLE IV

Plasma concentration of UDCA and GUDCA after an oral administration of this invention at a dose of 200 mg to three men

| | UDCA | | | | GUDCA | | | |
|---|---|---|---|---|---|---|---|---|
| Time(h) | #1 | #2 | #3 | mean | #1 | #2 | #3 | mean |
| 0.25 | 5.1202 | 10.9171 | 9.159 | 8.43 ± 1.69 | 0.1419 | 0.4549 | 0.3328 | 0.31 ± 0.09 |
| 0.5 | 4.4528 | 7.7432 | 7.4395 | 6.55 ± 1.05 | 0.2564 | 1.2455 | 0.864 | 0.79 ± 0.29 |
| 1 | 1.6921 | 1.546 | 0.2163 | 1.15 ± 0.47 | 0.2162 | 0.6926 | 0.2142 | 0.37 ± 0.16 |
| 1.5 | 0.5256 | 0.2759 | 0.168 | 0.32 ± 0.11 | 1.1573 | 0.1929 | 0.4752 | 0.61 ± 0.29 |
| 2 | 0.2349 | 0.2176 | 0.1227 | 0.19 ± 0.03 | 0.4013 | 0.0312 | 0.0657 | 0.17 ± 0.12 |
| 3 | 0.1237 | N.D. | 0.2074 | 0.17 ± 0.04 | 0.5085 | 0.4303 | 0.3315 | 0.42 ± 0.05 |
| 5 | | | | | 1.9205 | 0.0229 | 1.6311 | 1.18 ± 0.61 |
| 7 | | | | | 0.5328 | 0.4797 | 0.91 | 0.64 ± 0.14 |
| AUC (ug.h/ml) | 4.32 | 6.6 | 5.47 | 5.46 ± 0.66 | 6.26 | 2.22 | 4.65 | 4.38 ± 1.17 |
| Cmax (ug/ml) | 5.21 | 10.92 | 9.16 | 8.43 ± 1.69 | 1.92 | 1.25 | 1.63 | 1.6 |
| Tmax(h) | 0.25 | 0.25 | 0.25 | 0.25 | 5 | 0.5 | 5 | 3.5 ± 1.5 |

Pharmacokinetic parameters of UDCA in human after an oral administration of UDCA (M ± S.E.)

| | Cmax (ug/ml) | Tmax (hr) |
|---|---|---|
| Roda et al. (1994) | | |
| UDCA gelatine capsule, 450 mg | 2.59 | 3.8 |
| NaUDC gelatine capsule, 475 mg | 3.42 | 2.4 |
| NaUDC enteric-coated, 475 mg | 10 | 3.4 |
| Nagamatsu et al. (1997) | | |
| UDCA 200 mg | 1.9 ± 0.25 | 1.5 ± 0.4 |
| UDCA 400 mg | 7.09 ± 1.43 | 0.8 ± 0.2 |
| UDCA in this invention, 200 mg | 8.43 ± 1.69 | 0.25 |

TABLE III-6

| | Day | #1 | #2 | #3 | Average | Percentage |
|---|---|---|---|---|---|---|
| Ile | 0 | 0.292 | 0.282 | 0.287 | 0.287 | 100.0 |
| | 2 | 0.253 | 0.237 | 0.239 | 0.243 | 84.7 |
| | 5 | 0.221 | 0.212 | 0.221 | 0.218 | 76.0 |
| | 7 | 0.219 | 0.215 | 0.207 | 0.214 | 74.5 |
| | 9 | 0.206 | 0.192 | 0.207 | 0.202 | 70.2 |
| Leu | 0 | 0.507 | 0.495 | 0.509 | 0.504 | 100.0 |
| | 2 | 0.462 | 0.442 | 0.442 | 0.449 | 89.1 |
| | 5 | 0.429 | 0.428 | 0.427 | 0.428 | 85.0 |
| | 7 | 0.410 | 0.417 | 0.414 | 0.414 | 82.1 |
| | 9 | 0.417 | 0.377 | 0.418 | 0.404 | 80.2 |
| Val | 0 | 0.480 | 0.506 | 0.471 | 0.486 | 100.0 |
| | 2 | 0.536 | 0.478 | 0.504 | 0.506 | 104.2 |
| | 5 | 0.371 | 0.445 | 0.400 | 0.405 | 83.5 |
| | 7 | 0.384 | 0.384 | 0.424 | 0.397 | 81.8 |
| | 9 | 0.389 | 0.354 | 0.362 | 0.368 | 75.8 |

I claim:

1. An clear aqueous solution comprising:
   (a) a first material selected from the group consisting of a bile acid, an aqueous soluble derivative of a bile acid, a bile acid salt, and a bile acid conjugated with an amine by an amide linkage;
   (b) a second material selected from the group consisting of dextran and liquid glucose; and
   (c) water,
   wherein the first and second materials both remain in solution for all pH values of the solution within a selected range of pH values and wherein the weight ratio of the second material to the first material is less than about 30:1.

2. An clear aqueous solution comprising:
   (a) a first material selected from the group consisting of a bile acid, an aqueous soluble derivative of a bile acid, a bile acid salt, and a bile acid conjugated with an amine by an amide linkage;

(b) a second material selected from the group consisting of dextran and liquid glucose; and (c) water, wherein the first and second materials both remain in solution for all pH values of the solution within a selected range of pH values and wherein the concentration of the first material is more than about 1.17% (W/W).

3. An clear aqueous solution comprising:

(a) a first material selected from the group consisting of a bile acid, an aqueous soluble derivative of a bile acid, a bile acid salt, and a bile acid conjugated with an amine by an amide linkage;

(b) a second material selected from the group consisting of dextran and liquid glucose; and (c) water, wherein the first and second materials both remain in solution for all pH values of the solution within a selected range of pH values and wherein the concentration of the second material is more than about 35% (W/W).

4. The aqueous solution of any one of claims 1, 2 or 3 wherein the first material is present in a pharmaceutically effective amount.

5. The aqueous solution of any one of claims 1, 2 or 3 wherein the solution additionally comprises a pharmaceutically effective amount of a pharmaceutical compound and the pharmaceutical compound remains in solution for all pH values within the selected range.

6. The aqueous solution of claim 5 wherein the pharmaceutical compound is selected from the group consisting of insulin, heparin, calcitonin, ampicillin, amantadine, rimantadine, sildenafil, apomorphine, yohimbin, trazodone, ribavirin, neomycin sulfate, paclitaxel and its derivatives, retinol and tretinoin.

7. The aqueous solution of claim 5 wherein the first material is ursodeoxycholic acid and the pharmaceutical compound is selected from the group consisting of metformin HCl, ranitidine HCl, cimetidine, lamivudine, cetrizine 2HCl, amantadine, rimantadine, sildenafil, apomorphine, yohimbine, trazodone, ribavirin, dexamethasone, hydrocortisone, prednisolone, triamcinolone, cortisone, niacin, catechin and its derivatives, taurine, vitamins, and naturally occurring amino acids.

8. The aqueous solution of any one of claims 1, 2 or 3 wherein the selected pH range is between approximately 1 and approximately 10 inclusive.

9. The aqueous solution of anM one of claims 1, 2 or 3 wherein the selected pH range is the range spanned by the prevailing pH values found in the mouth, stomach, and intestines of a mammal.

10. The aqueous solution of any one of claims 1, 2 or 3 wherein the selected pH range is the range spanned by the prevailing pH values found in the mouth, stomach, and intestines of a human being.

11. The aqueous solution of any one of claims 1, 2 or 3 wherein the selected pH range is a range of pH values obtainable in an aqueous system encountered by the solution duiing preparation, administration and until absorption in the body to which the solution is administered.

12. The aqueous solution of any one of claims 1, 2 or 3 wherein the selected pH range spans all obtainable pH values in an aqueous system.

13. The aqueous solution of any one of claims 1, 2 or 3 wherein the first material is selected from the group consisting of ursodeoxycholic acid, chenodeoxycholic acid, cholic acid, hyodeoxycholic acid, deoxycholic acid, 7-oxolithocholic acid, lithocholic acid, iododeoxycholic acid, iocholic acid, tauroursodeoxycholic acid, taurochenodeoxycholic acid, taurodeoxycholic acid, glycoursodeoxycholic acid, taurocholic acid, glycocholic acid, their derivatives at a hydroxyl or carboxylic acid group on the steroid nucleus, their salts, or their conjugates with amines.

14. The aqueous solution of anM one of claims 1 or 2 wherein the bile acid salt is a product of the reaction of a bile acid and an amine.

15. The aqueous solution of claim 14 wherein the bile acid is selected from the group consisting of ursodexycholic acid, chenodeoxycholic acid, cholic acid, hyodeoxycholic acid, deoxycholic acid, 7-oxolithocholic acid, iododeoxycholic acid, iocholic acid, tauroursodexycholic acid, glycocholic acid, and their derivates at a hydroxyl or carboxylic acid group on the steroid nucleus.

16. The aqueous solution of claim 14 wherein the amine is selected from the group consisting of an aliphatic free amine, trintine, dietylene triamine, tetraethylene pentamine, a basic amino acid, arginine, lysine, lysine, ornithine, ammonia, an amino sugar, D-glucamine, N-alkylglucamines, a quaternary ammonium derivative, choline, an heterocyclic amine, piperazine, N-alkylpiperazine, piperidine, N-alkylpiperidine, morpholine, N-alkylmorphline, pyrrolidine, triethanolamnine, and trimethanolaminie.

17. The aqueous solution of any one of claims 1, 2 or 3 wherein the bile acid salt is a soluble metal salt of a bile acid or an aqueous soluble O-sulfonated bile acid.

18. The aqueous solution of anM one of claims 1, 2 or 3 wherein the second material is the product of partial or incomplete hydrolysis of a starch.

19. The aqueous solution of claim 18 wherein the starch is selected from the group consisting of maltodextri, dextrin, dextran, liquid glucose, and soluble starch.

20. The aqueous solution of claim 5 wherein the first material is an adjuvant.

21. The aqueous solution of claim 5 wherein the first material is a carrier of the pharmaceutical compound.

22. The aqueous solution of any one of claims 1, 2 or 3 wherein the solution further comprises a micelle forming material.

23. The aqueous solution of any one of claims 1, 2 or 3 wherein the solution is comprised in a preparation for oral consumption.

24. The aqueous solution of any one of claims 1, 2 or 3 wherein the solution is comprised in an enema.

25. The aqueous solution of any one of claims 1, 2 or 3 wherein the solution is comprised in a mouthwash.

26. The aqueous solution of any one of claims 1, 2 or 3 wherein the solution is comprised in a gargle.

27. The aqueous solution of any one of claims 1, 2 or 3 wherein the solution is comprised in a preparation for nasal administration.

28. The aqueous solution of any one of claims 1, 2 or 3 wherein the solution is comprised in a preparation for otic administration.

29. The aqueous solution of any one of claims 1, 2 or 3 wherein the solution is comprised in an injection.

30. The aqueous solution of any one of claims 1, 2 or 3 wherein the solution is comprised in a douche.

31. The aqueous solution of any one of claims 1, 2 or 3 wherein the solution is comprised in a topical skin preparation.

32. The aqueous solution of any one of claims 1, 2 or 3 wherein the solution is comprised in a cosmetic preparation.

33. A method of preparing an aqueous solution wherein the solution forms no precipitate at any pH value of the solution within a selected range of pH values comprising:

(a) dissolving a bile acid, bile acid salt, or bile acid-amine conjugate in water to form a clear solution;
(b) adding an aqueous soluble starch conversion product to the clear solution and allowing it to dissolve to form a clear solution; and
(c) optionally adding a pharmaceutically effective amount of a pharmaceutical compound.

34. The method of claim 33 wherein the selected range is all pH values obtainable in an aqueous system.

35. The method of claim 33 wherein the selected range is between approximately pH 1 and approximately pH 10.

* * * * *